US010143355B2

(12) United States Patent
Gomez et al.

(10) Patent No.: US 10,143,355 B2
(45) Date of Patent: Dec. 4, 2018

(54) INSTRUMENT SLEEVE STRENGTHENING DEVICE

(71) Applicants: Ricardo Alexander Gomez, Light House, FL (US); Sandy Lawrence Heck, Los Angeles, CA (US); Eric William Conley, South Berwick, ME (US)

(72) Inventors: Ricardo Alexander Gomez, Light House, FL (US); Sandy Lawrence Heck, Los Angeles, CA (US); Eric William Conley, South Berwick, ME (US)

(73) Assignee: INNERSPACE SURGICAL CORPORATION, Pompano Beach, FL (US)

(*) Notice: Subject to any disclaimer, the term of this patent is extended or adjusted under 35 U.S.C. 154(b) by 284 days.

(21) Appl. No.: 15/062,706

(22) Filed: Mar. 7, 2016

(65) Prior Publication Data

US 2016/0256036 A1      Sep. 8, 2016

Related U.S. Application Data

(60) Provisional application No. 62/129,743, filed on Mar. 6, 2015.

(51) Int. Cl.
  *A61B 1/00* (2006.01)
  *A61B 90/00* (2016.01)
  *A61B 1/313* (2006.01)
  *A61B 17/00* (2006.01)
  *A61B 17/29* (2006.01)
  *A61B 17/34* (2006.01)

(52) U.S. Cl.
  CPC ...... *A61B 1/00078* (2013.01); *A61B 1/00135* (2013.01); *A61B 1/00147* (2013.01); *A61B 1/3132* (2013.01); *A61B 17/00234* (2013.01); *A61B 17/29* (2013.01); *A61B 90/03* (2016.02); *A61B 2017/00336* (2013.01); *A61B 2017/00991* (2013.01); *A61B 2017/2901* (2013.01); *A61B 2017/3407* (2013.01); *A61B 2017/3492* (2013.01); *A61B 2090/036* (2016.02)

(58) Field of Classification Search
  CPC .. A61B 90/03; A61B 1/00078; A61B 1/00135
  See application file for complete search history.

(56) References Cited

U.S. PATENT DOCUMENTS

| | | | | |
|---|---|---|---|---|
| 2,421,354 A | * | 5/1947 | Reiter | A61C 3/08 433/151 |
| 5,009,661 A | * | 4/1991 | Michelson | A61B 17/1608 606/170 |
| 5,021,059 A | * | 6/1991 | Kensey | A61B 17/0057 604/15 |

* cited by examiner

*Primary Examiner* — Christian Sevilla
(74) *Attorney, Agent, or Firm* — Grogan, Tuccillo & Vanderleeden, LLP (57) ABSTRACT

The present invention is directed towards surgical devices and a method used in minimally invasive surgery whereby a device is incorporated into or onto an instrument to strengthen its shaft and improve its functionality in minimally invasive surgery. The primary goal of the invention is to increase the strength and rigidity of an instrument by using a specially designed sleeve that strengthens the instrument, thereby reducing its ability to bend and increasing its load carrying capacity. The invention will provide a system that gives extra strength and rigidity to small instrument shafts, so that surgeons can still safely and reliably perform their procedures, but can also use incisions that are as small as possible.

16 Claims, 12 Drawing Sheets

INSTRUMENT SLEEVE STRENGTHENING DEVICE

CROSS-REFERENCE TO RELATED APPLICATIONS

This application claims the benefit of U.S. Provisional Application Ser. No. 62/129,743, filed on Mar. 6, 2015, which is herein incorporated by reference in its entirety.

FIELD OF INVENTION

The present application is directed toward medical instruments and, more particularly, to a specialized medical strengthening sleeve used in minimally invasive surgery.

BACKGROUND OF INVENTION

Laparoscopy is a surgical procedure performed through small incisions in the abdomen whereby a trocar device is inserted to provide a means for passage of medical instruments. A thin cylindrical instrument called a laparoscope, connected to a camera, is then used to provide a clear picture of the abdominal cavity to the surgeon.

In particular, prior to starting a surgical procedure a small incision is made in the abdominal wall of the patient whereby a trocar/cannula device is inserted. Trocar device diameters range in size from 5 to 12 mm and provide a clear passage for the introduction of medical devices into the abdomen. Once the abdominal opening is secured, a laparoscope is inserted thru the trocar opening permitting the surgeon to view the abdominal cavity space. Typically, several additional incisions are made ranging in size from 5-12 mm for the introduction of other medical devices. A device called an insufflator is also used; its purpose is to inflate the abdominal cavity area with carbon dioxide and create space. The space created provides a greater working and viewing area for the surgeon.

Minimally invasive surgeries such as laparoscopies may provide a host of benefits as compared to traditional surgeries using large incisions, including lower operating cost, less patient trauma, less scarring, less pain, lower surgical complications, quicker recovery times, shortened hospital stays, and less chance of infection.

As the field of minimally invasive surgery continues evolving, less invasive techniques are desired. The need for smaller laparoscopic tools has also arisen. In recent years, a newer version of laparoscopy has evolved called needlescopic surgery. Needlescopic surgery is a progression of laparoscopic surgery whereby incisions smaller than 3 millimeters are made. Virtually no scarring occurs, pain is reduced, and recovery times are faster. However the problem associated with this new type of procedure is the limited functionality of the insertion instrument. As the instruments became thinner, the heads of the instruments became smaller and less effective to manipulate tissues and organs. For this reason among others, needlescopic surgery has not been widely adopted by the surgical community.

Another new type of surgery called Single Incision Laparoscopic Surgery (SILS) has also been tried to reduce the number of incisions related to surgery. The concept is that a single incision is made at the umbilicus allowing a specialized tool to be placed at the opening. The opening allows the insertion of several very small instrument tools into the abdomen. The problems associated with this procedure are first in the level of complexity for each procedure versus the traditional laparoscopic procedure, the lack of functionality of the smaller tools, and the very tight working area. It is usually limited to only 3 very small instrument devices which often lack the full functionality required by traditional surgeons.

Another new type of surgery used today is called Natural Orifice Translumenal Endoscopic Surgery (NOTES). It basically involves placing a flexible endoscope through one of the body's natural orifices, like the mouth, anus, vagina, or urethra. Its purpose is to achieve access to a space near the affected area. Some of the problems associated with this type of surgery are that the number of instrument heads used is usually limited to only one, not all areas of the body are accessible, and since most views are two dimensional there are special orientation problems.

An additional problem associated with both Single Incision Laparoscopic Surgery (SILS) and Natural Orifice Translumenal Endoscopic Surgery (NOTES) is the inability to achieve triangulation. Triangulation in this instance can be defined as the ability to come at a target from different directions or angles. Triangulation provides significant benefits to the surgeon, among them are: effective control of the surgical procedure and the ability to better manipulate internal body parts. When this ability is lost it is difficult to effectively perform these types of surgeries. This is one of the reasons that have prevented SILS and NOTES from being widely adopted.

People have experimented with the concept of attaching larger instrument heads to thin shafts inside the body, but no effective method has been developed or invented to facilitate the insertion and attachment of such instrument heads within the body, especially under direct visualization.

It has been a long term goal of minimally invasive surgeons to perform surgery with the absolute smallest incisions while providing the means of visualization of the intended area. Therefore there is a need in the field for a means of effectively attaching and securing full-sized laparoscopic instrument heads to small diameter instrument shafts within the body while under direct visualization. This need would minimize the number and size of incisions performed for each procedure. The challenge with this approach is that the current methods used require additional trocar/cannula openings.

In laparoscopic surgery, incisions are made ranging from 5-12 mm and usually require up to 4 separate incisions. In the specialized field of needlescopic surgery the instrument heads are often too small and lack functionality. Visualization of the attachment process is also a problem that has limited the internal attachment process to an external one. The challenge has been in finding a means of inserting, removing and remotely attaching a normal sized medical instrument head inside the abdomen of a patient. The benefits are numerous to the patient including; reduced scarring, quicker recovery times, less chance of infections, and lower morbidity risks associated with infections. The advantages to the surgeon are better handling, and better functionality of the instrument heads, often a trade off that is associated with smaller instrument heads.

As newer technologies continue to evolve, there is a need in the field for smaller tools having better rigidity and strength characteristics. In U.S. Provisional Application Ser. No. 62/093,789, filed on Dec. 18, 2014, entitled "Method and Apparatus for Securing Laparoscopic Instrument Heads in the Abdomen Under Direct Visualization", which is hereby incorporated by reference herein in its entirety, a new technology was disclosed whereby thin shafts having diameters measuring between 1-4 mm are introduced into a patient's body. As elongated instruments continue to reduce in diameter, however, rigidity of such instruments can become problematic. In particular, the further such instruments are extended the weaker they become. Therefore it is the goal of this invention to provide a means of providing rigidity and enhanced strength to elongated medical instruments by the introduction of a strengthening sleeve device.

These and other aspects, features and advantages of the present invention will become more readily apparent from the attached drawings and the detailed description of the preferred embodiments which follow.

SUMMARY OF INVENTION

The present invention is directed towards surgical devices and a method used in minimally invasive surgery whereby a device is incorporated into or onto an instrument to strengthen its shaft and improve its functionality in minimally invasive surgery. The primary goal of the invention is to increase the strength and rigidity of an instrument by using a specially designed sleeve that strengthens the instrument, thereby reducing its ability to bend and increasing its load carrying capacity.

Medical device manufacturers aim to reduce medical instrument shaft diameters so that they can reduce the size of the skin incisions, but this has resulted in small diameter instrument shafts that can bend or break easily. The goal of this invention is to provide a system that gives extra strength and rigidity to those small instrument shafts, so that surgeons can still safely and reliably perform their procedures, but can also use incisions that are as small as possible.

The strengthening sleeve device is an assembly that can be attached onto an instrument, or be incorporated into one. It incorporates a collapsible tube assembly, which surrounds the smaller diameter instrument shaft and imparts extra strength to resist bending. The strengthening sleeve covers the part of the instrument shaft that is outside of the body during laparoscopic procedures. As the instrument is pushed into the body and pulled out of the body during minimally invasive surgical procedures, the strengthening sleeve will collapse or expand as the instrument moves, such that it covers the entire part of the instrument shaft that is outside the body at any given time. Since the larger diameter strengthening sleeve always remains over the part of the instrument that is outside the body, and does not enter or interfere with the skin incision, the incisions can remain as small as possible. The assembly may also include a manually adjustable locking knob, a proximal end spring retainer, an elongated spring, a collapsible tube assembly, a distal end spring retainer, a swivel ball joint assembly, a foot device, an adhesive pad, and suture holes.

The sleeve device is attached to the outer shaft of a medical instrument so that as the instrument is moved in or out, the sleeve device also collapses or extends. This collapse and extension of the strengthening sleeve can be achieved manually or in an automatic fashion, relying on springs, weights, an anchored base, or any other method that would allow the strengthening sleeve to adjust its length along with the instrument's movement. In one embodiment, springs are used to maintain full coverage of the strengthening sleeve over the part of the shaft outside the body. For example, as pressure is applied forward on an instrument handle the strengthening sleeve compresses itself resulting in the shortening of the strengthening sleeve and the physical movement of the shaft further into the body.

The instrument strengthening sleeve device covers the instrument from the proximal part of the shaft, near the handle, down to the foot device at the distal end of the strengthening sleeve. The foot device remains in contact with the skin at all times, and can be slid there manually or held there with the assistance of an adhesive pad, sutures through holes in the foot device, springs which apply a force against the foot device, weights, or any other mechanism that would keep the foot device in contact with the skin, thereby making sure that the strengthening sleeve covers all of the instrument shaft that is outside the body, right down to the skin. There is no specific foot size required with the exception that it must prevent the sleeve from passing through the incision into the abdomen.

The strengthening sleeve locking knob can be used to lock the strengthening sleeve into a specific length. This can be used to hold an instrument in place or to limit the distance that the instrument can be inserted into the body, which can provide extra safety when initially inserting instruments into the body or when executing careful actions within the body, such as mating instrument heads to instrument shafts.

The telescoping collapsible tubes that make up the strengthening sleeve can be configured of two or more parts. Its construction can be of titanium, metal alloys, plastics, stainless steel, or not limited to but including any other industry standard materials.

It should be noted that in similar embodiments the compression of the elongated spring provides additional rigidity and strength to the instrument shaft. This is accomplished by the compression action of the spring(s), forming a wall, further limiting the movement of the shaft that is outside the patient but inside the tube assembly.

According to an aspect of the invention, the instrument sleeve strengthening device is adapted to strengthen the shaft of an instrument extending sleeve by applying a biasing force to the shaft of the instrument. The instrument sleeve strengthening device may be directly coupled to a proximal part of the instrument, to a port, or may be coupled directly to a patient, and may be permanently coupled to the instrument or manually coupled to the instrument as needed. The instrument sleeve strengthening device also includes a mechanism which applies an equalizing force to the tubular member and is adjustable. As the surgical instrument is extended through the opening the medical instrument is further stabilized by the axial force applied by a ballast spring or other feature.

These and other aspects of the present invention will become more readily apparent from the attached drawings and the detailed description of the preferred embodiments which follow.

BRIEF DESCRIPTION OF DRAWINGS

The present invention will be better understood from reading the following description of non-limiting embodiments, with reference to the attached drawings, wherein below.

Like reference numerals refer to like parts throughout the several views of the drawings. While the various features of this invention are hereinafter described and illustrated as being particularly adapted for providing rigidity to medical instrument devices the invention is not limited to the embodiments illustrated in the drawings but are merely used to illustrate the wide variety of uses of this invention. Therefore, the foregoing is considered as illustrative only of the principles of the invention. Since numerous modification and changes will readily occur by those skilled in the art, it is not desired to limit the invention to the exact construction and operation shown and described and accordingly, all suitable modifications and equivalents may be resorted to, falling within the scope of the invention.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
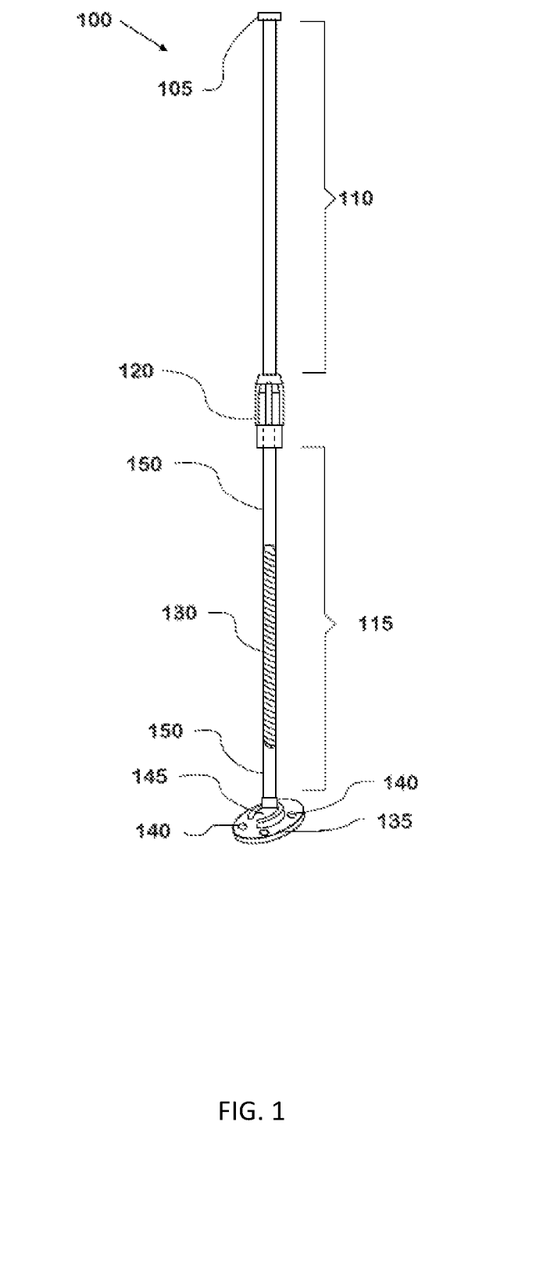
FIG. 1 is a perspective view of a strengthening device for a medical instrument, according to an embodiment of the present invention.
Figure 2:
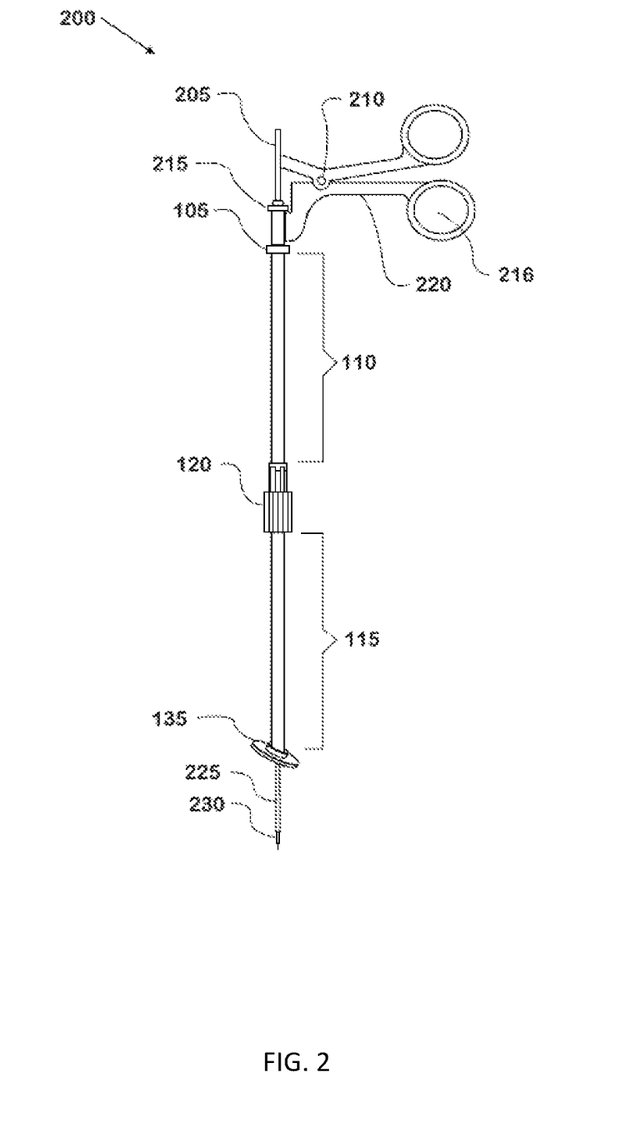
FIG. 2 is a perspective view of the strengthening device of FIG. 1, shown fully attached to a medical instrument.
Figure 3:
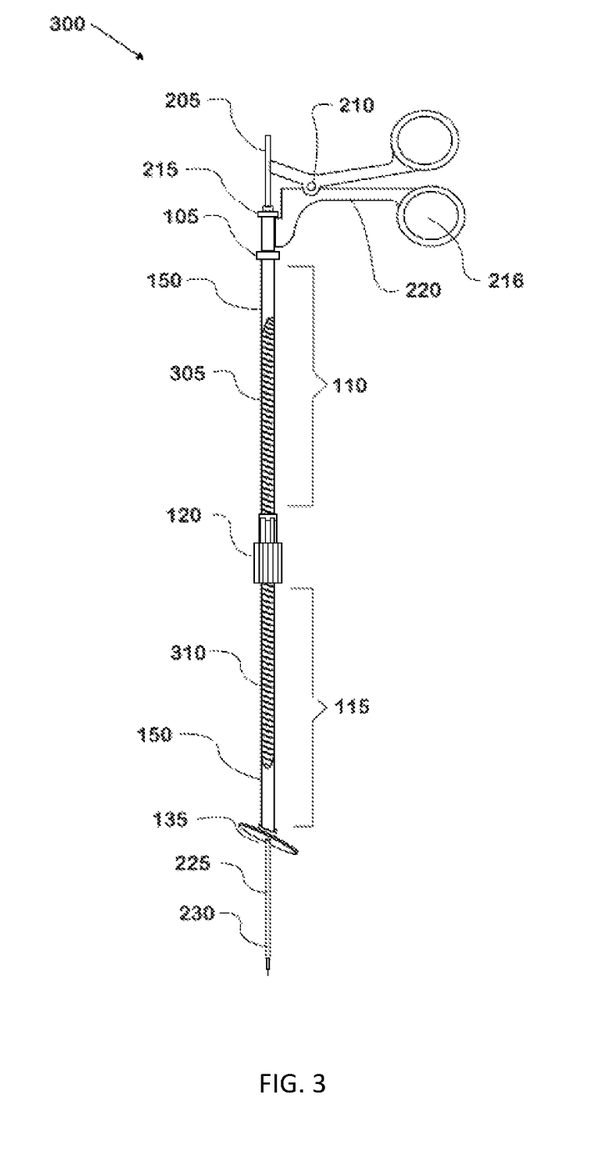
FIG. 3 is an elevational view of the strengthening device and medical instrument of FIG. 2.
Figure 4:
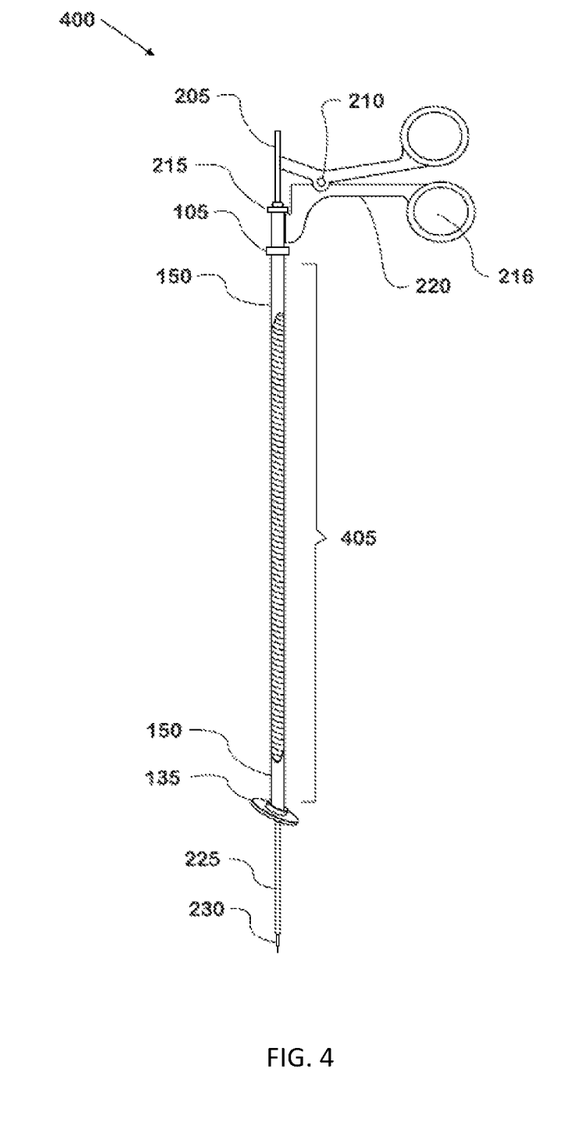
FIG. 4 is a perspective, partial cross-sectional view of the strengthening device.

With respect to FIG. 1 an isometric view of an exemplary strengthening device or sleeve 100 for an instrument shaft is illustrated. The strengthening device 100 generally includes an attachment mechanism 105 used to attach the device to a medical instrument or device (not shown). As will be described in greater detail hereinafter, the strengthening device 100 includes an upper tube 110 and a lower tube 115 which may enclose one or two elongated spring 130, depending on the desired usage. In the embodiment illustrated in FIG. 1, only the lower tube 115 is illustrated as containing an elongated spring 130. The upper and lower tubes 110, 115 are collapsible tubes or conduits which permit their shortening in total length when compressed. In an embodiment, the tubes 110, 115 are telescoping in nature. They may also be composed of more than two tubes, permitting considerable shortening in length.

As further illustrated in FIG. 1, the device 100 also includes a locking assembly 120 that connects the upper and lower tubes 110, 115 to one another, and which permits adjusting of the length of elongated spring(s) within the tubes, respectively. A swivel ball joint assembly 145 located at the distal end of the lower tube 115 permits pivoting and provides a flexible means of obtaining a desirable entry angle to the surgeon. Attached to the swivel ball joint assembly 145 is a foot 135 which, during use, is placed on the patient near the percutaneous area to restrain the device 100 from sliding inside the patient, as discussed in detail hereinafter. As will be readily appreciated, therefore, the ball joint 145 permits pivoting movement of the foot 135 relative to the lower tube 115 so that device 100 may be stabilized in any orientation. Adjacent to the periphery of the foot 135 are generally equally spaced suture holes 140 are that may be used to physically attach the foot 135 to the patient. In an embodiment, the foot 135 may also, or alternatively, be provided with an adhesive material on its bottom side, allowing the foot 135 to be adhered to a patient's skin.

Turning now to FIGS. 2-5, the strengthening device 100 is shown fully attached to a medical instrument (e.g., a laparoscopic tool) having a handle assembly 220 attached to an elongate shaft 205. In particular, as shown therein, attachment mechanism 105 of the device 100 is used to attach the instrument handle assembly 220 to the strengthening device 100. Pivot point 210 of the handle assembly is used to move a proximal end of the instrument shaft 205. Two instrument handle finger inserts 216 are used to manually control the movement of handle assembly 220. An instrument shaft locking knob 215 permits the instrument shaft 205 to be securely held. The upper tube 110 and lower tube are attached and held in place by the locking assembly 120. By adjusting the locking knob 215 compression on the tube assembly is adjusted. As shown therein, when attached the strengthening device 100, the instrument shaft 205 extends through the upper and lower tubes 110, 115 of the device 100. A distal end 225 of the shaft 205 protrudes from the lower tube 115 and terminates in an instrument tip 230. The instrument tip is used to perforate the skin and provide a means for the distal end 225 of the shaft 205 to enter the abdomen of the patient.

Figure 5:
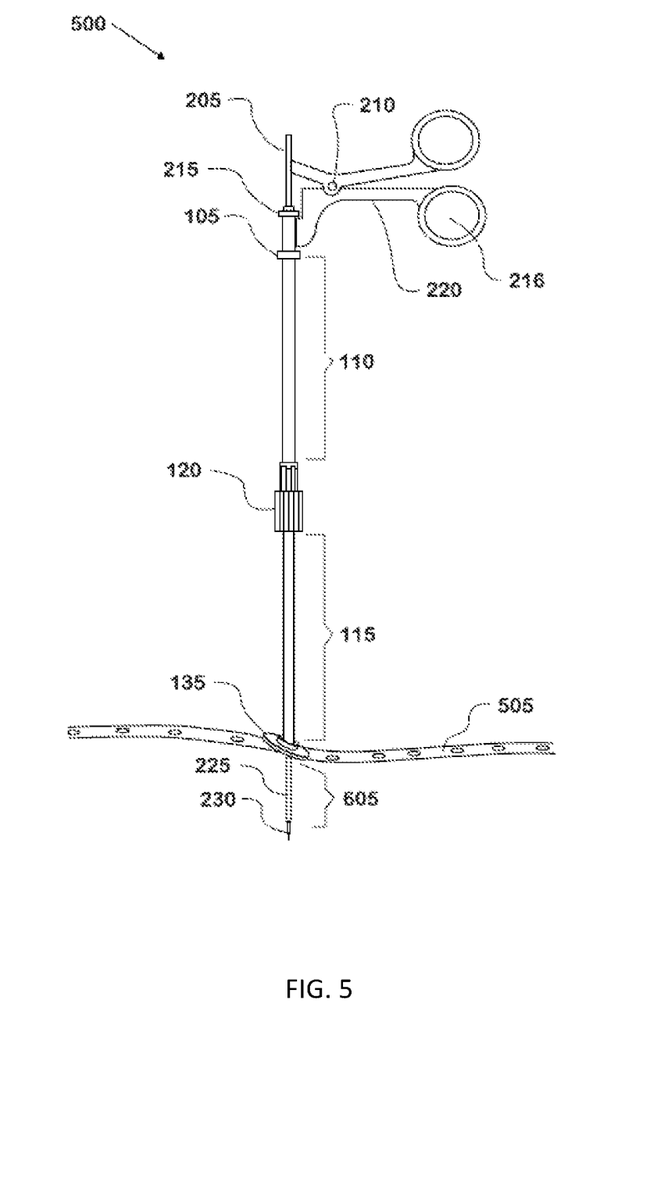
FIG. 5 is a cross-sectional view of the strengthening device, taken along line A-A of FIG. 4.
Figure 6:
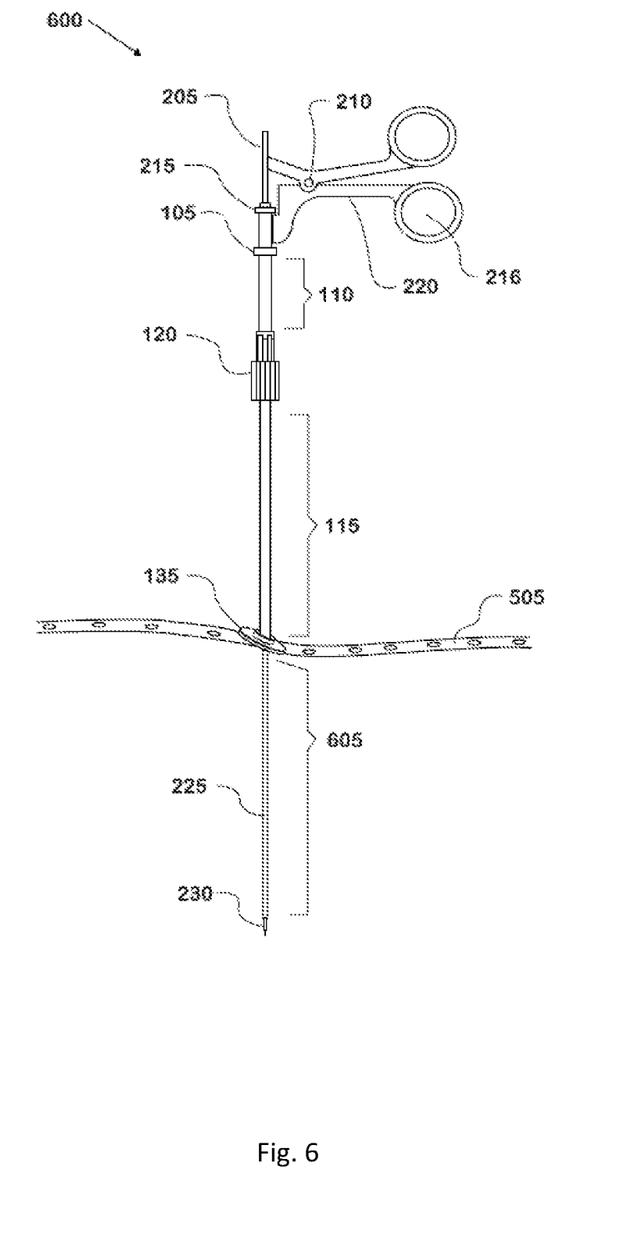
FIG. 6 is a perspective view of the strengthening device in FIG. 1, shown in an uncompressed position.
Figure 7:
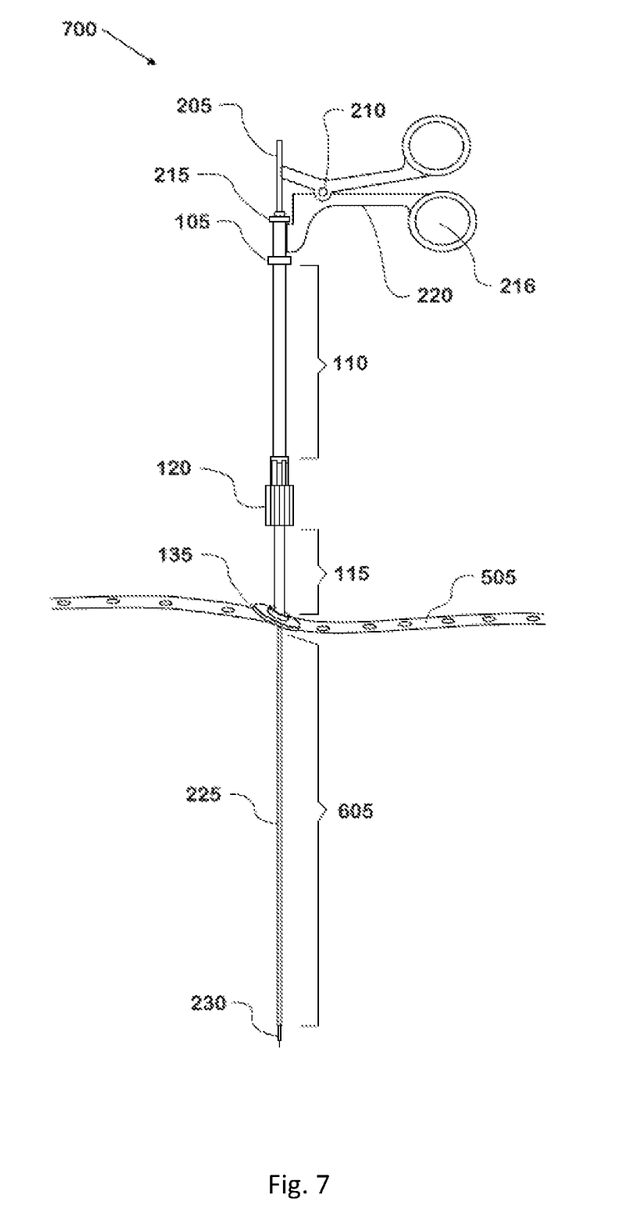
FIG. 7 is a perspective view of the strengthening device of FIG. 1, shown in a compressed position, providing rigidity to an instrument shaft.

Turning now to FIGS. 6 and 7, operation of the strengthening device is illustrated, with FIG. 5 depicting the strengthening device 100 in its uncompressed position. As shown therein, once the medical device (e.g., a laparoscopic tool) is attached to the device 100, the instrument tip 230 on the distal end 225 of instrument shaft 205 is utilized to perforate the skin 505 of a patient. Typically the device 100 is initially held with two hands as it is positioned on the patient. The instrument tip 230 is percutaneously passed through a patient's abdomen and stops when the foot 135 presses against the skin or trocar. As discussed above, foot 135 prevents the device 100 from entering the percutaneous area 505. The foot 135 may be secured to the patient to prevent movement of the device 100 utilizing an adhesive pad or through the use of sutures provided through apertures 140. In particular, at his point the surgeon has the option of attaching sutures to the foot 135 through openings 140 to secure the device to the patient, or can expose an adhesive surface on the underside of the foot 135. The foot 135 also pushes back on the lower tube 115, thus providing a compression force to the elongated spring housed within the lower tube 115. The exposed distal shaft 605 is in its normal position in FIG. 6. The extent to which the tip 230 of the shaft 205 initially protrudes into the body of the patient (in the uncompressed position) may be adjusted by moving the locking assembly 120 upward or downward (e.g., by rotating). In connection with this, the locking assembly 120 permits the upper tube assembly 110 and lower tube assembly 115 to be held in place at desired lengths through a tightening means. In an embodiment, the tightening means may consist of rotating fixed attachment that can be adjusted by the operator.

With reference to FIG. 7, when it is desired to insert the instrument tip 230 further into the patient, pressure is applied at the instrument handle assembly 220. In particular, when further reach is required by the surgeon, pressure is applied to the handle assembly 220 and distal portion 225 of the shaft 205 is extended further out. The compression of the elongated spring 130 inside the tube 115 can provide extra support to the shaft, further increasing its strength and rigidity. Indeed, the pressure applied is transferred to both the upper and lower tubes 110, 115. Since the elongated spring is housed within the lower tube 115, the lower elongated spring 130 compresses, permitting the distal end 225 of the shaft 205 to extend outwards and into the patient. As the lower tube 115 compresses in size, the exposed distal shaft 605 expands directly proportional to the distance moved by the compression of the lower tube 115. Importantly, the large diameter sleeve (i.e., tubes 110, 115 and elongated spring 130) surrounds the small diameter instrument shaft 205, thereby increasing its strength, rigidity and load carrying capacity by adding support and reducing the instrument's ability to bend.

Figure 8:
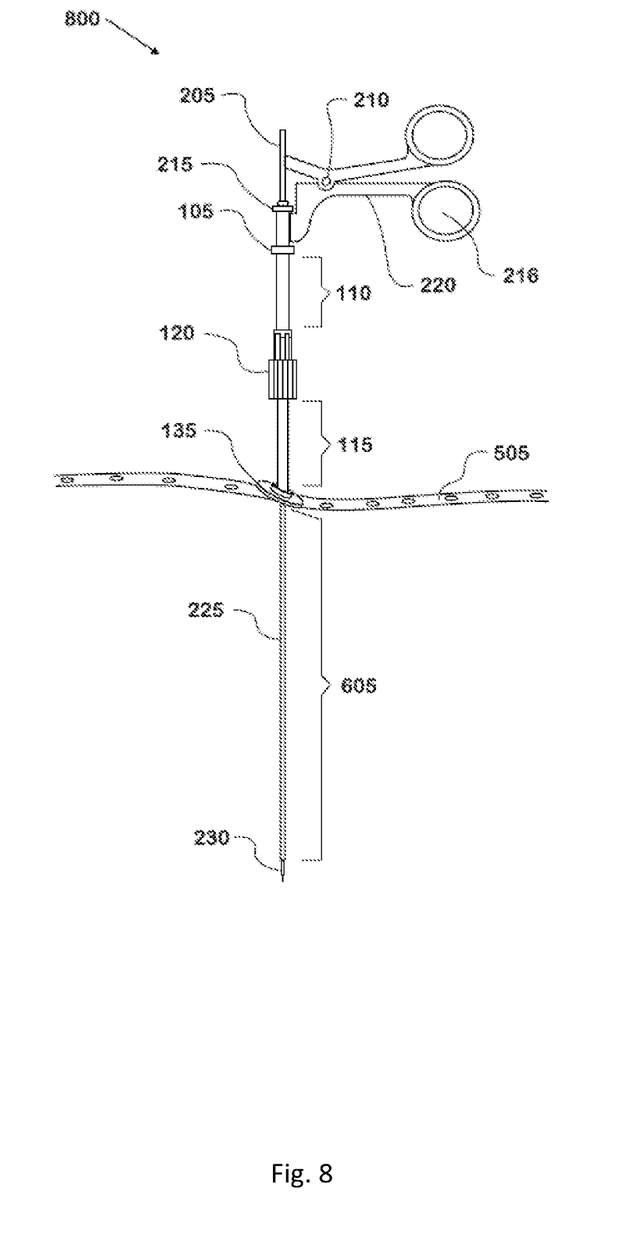
FIG. 8 is a perspective view of a strengthening device according to another embodiment of the present invention, shown in a compressed position, providing rigidity to an instrument shaft.

Referring now to FIG. 8, a strengthening device 400 having an elongated spring within the upper tube 110 is illustrated in use. The instrument tip 230 may be inserted into a patient and the device 400 secured to the body of a patient in the manner described above. When it is desired to insert the instrument tip 230 further into the patient, pressure is applied at the instrument handle assembly 220, thus compressing the elongated spring and collapsing the upper tube 110. As the upper tube 110 compresses in size, the exposed distal shaft 605 expands directly proportional to the distance moved. As indicated, the tubes 110, 115 and elongated spring within the upper tube 110) surrounds the small diameter instrument shaft 205, thereby increasing its strength, rigidity and load carrying capacity by adding support and reducing the instrument's ability to bend.

Figure 9:
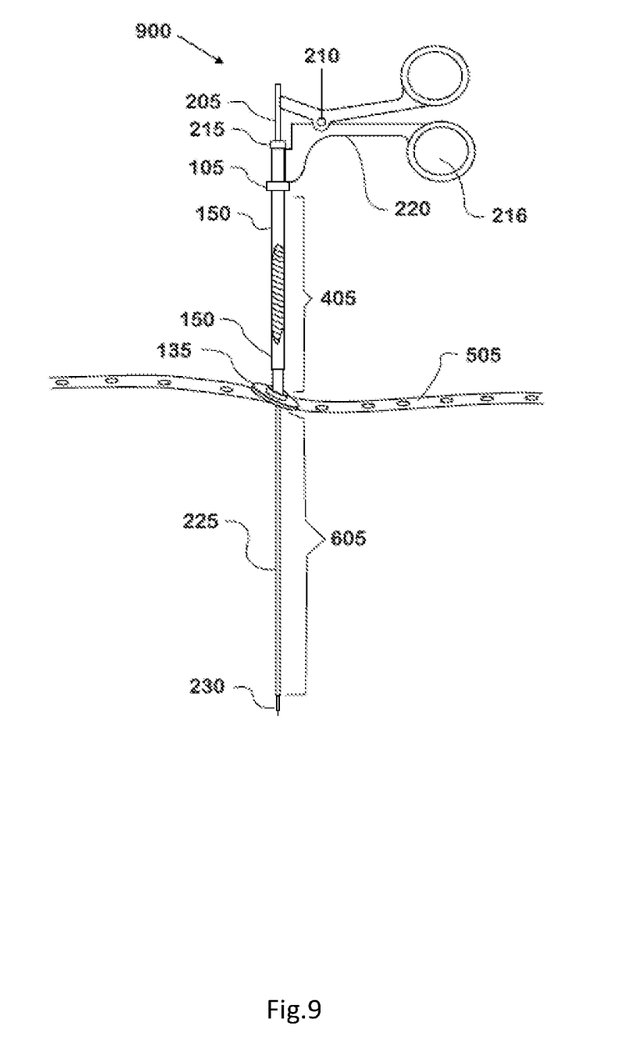
FIG. 9 is a perspective view of a strengthening device according to another embodiment of the present invention.

With respect to FIG. 9 an isometric view of a strengthening device 300 for an instrument shaft according to another embodiment of the invention is illustrated. Strengthening device 300 is substantially similar to strengthening device 100, where like reference numerals designate like parts. As shown therein, both the upper tube 110 and lower tube 115 house elongated springs 305, 310, respectively, therein. The use of two elongated springs 305, 310 in the upper and lower tubes 110, 115 provide a greater degree of rigidity and strength to the medical device and, more particularly, to the shaft 205 of the medical device, as discussed in detail below. As illustrated in FIG. 6, the elongated springs 305, 310 are preferably fully contained within the upper and lower tubes 110, 115. The tubes 110, 115 are collapsible and/or compressible to conform to the elongated springs 305, 310. The telescoping tubes are also collapsible. Typically the upper spring 305 slides into the upper tube 110 and is retrained between the locking assembly 120 and the attachment mechanism 105. Lower spring 310 slides into the lower tube 115 and is retained between the locking assembly 120 and the swivel ball joint assembly 145. In particular, the elongated springs 305, 310 are held in place by the force they apply at their respective ends.

Figure 10:
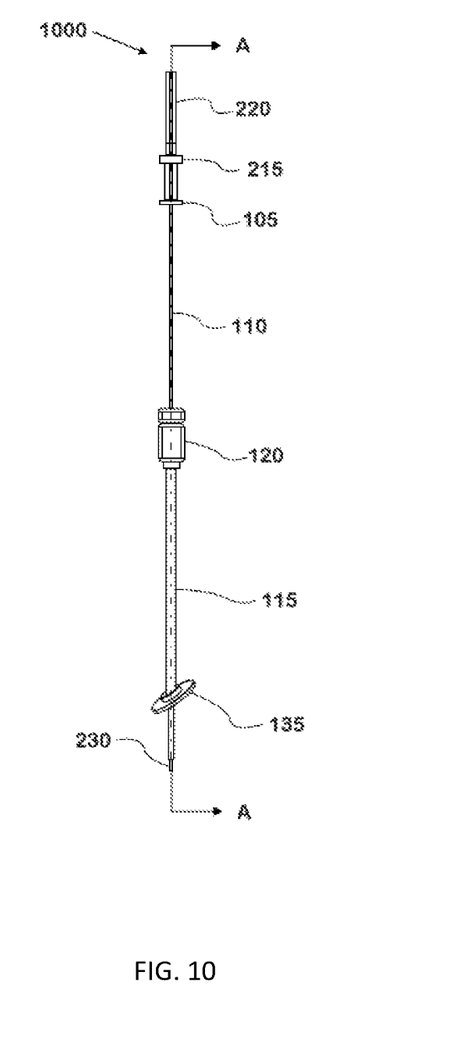
FIG. 10 is a perspective view of the strengthening device of FIG. 9, shown in a compressed position, providing rigidity to an instrument shaft.

Referring now to FIG. 10, in operation, as both collapsible tubes 110, 115 are compressed by the force exerted on them by the instrument handle assembly 220, they begin to compress to a smaller length. In particular, as the upper and lower tubes 110, 115 compresses in size, their combined compression distance (i.e., shortening) corresponds with the extra distance the exposed distal shaft 605 travels into the patient. Importantly, during this compression, the tubes 110, 115 and elongated springs 305, 310 surround the small diameter instrument shaft 205, thereby increasing its strength, rigidity and load carrying capacity by adding support and reducing the instrument's ability to bend.

Figure 11:
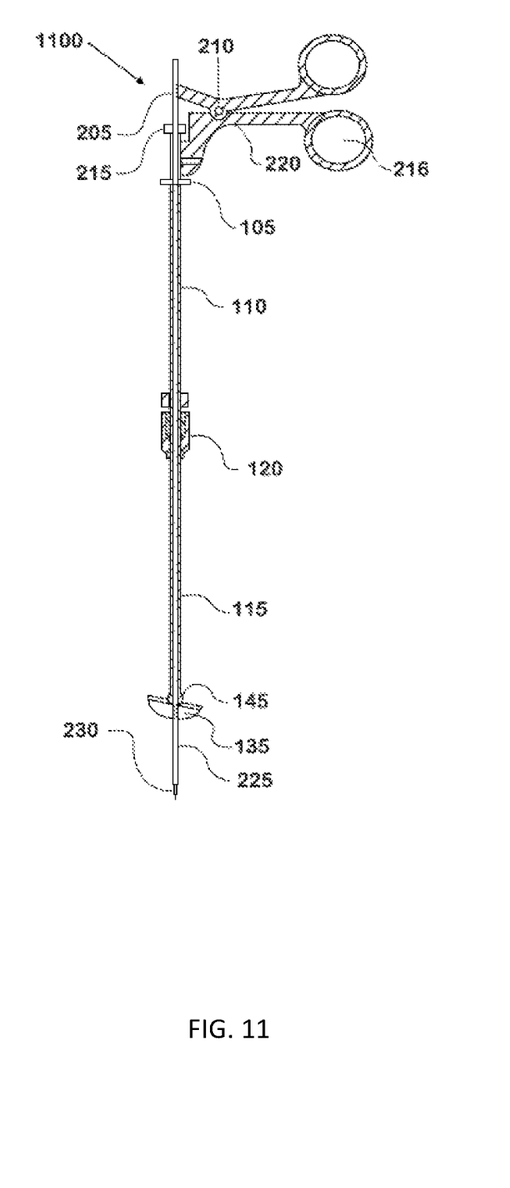
FIG. 11 is a perspective view of a strengthening device according to yet another embodiment of the present invention.

With respect to FIG. 11 an isometric view of a strengthening device 500 for an instrument shaft according to yet another embodiment of the present invention is illustrated. The strengthening device 500 is generally similar to the device 100 described above, where like reference numerals designate like parts. However, as shown therein, the device 500 includes a single collapsible tube 150 that extends from the foot 135 to the attachment mechanism 105 (rather than upper and lower tubes). In this embodiment, a single elongated spring 405 is housed within the tube 150.

Figure 12:
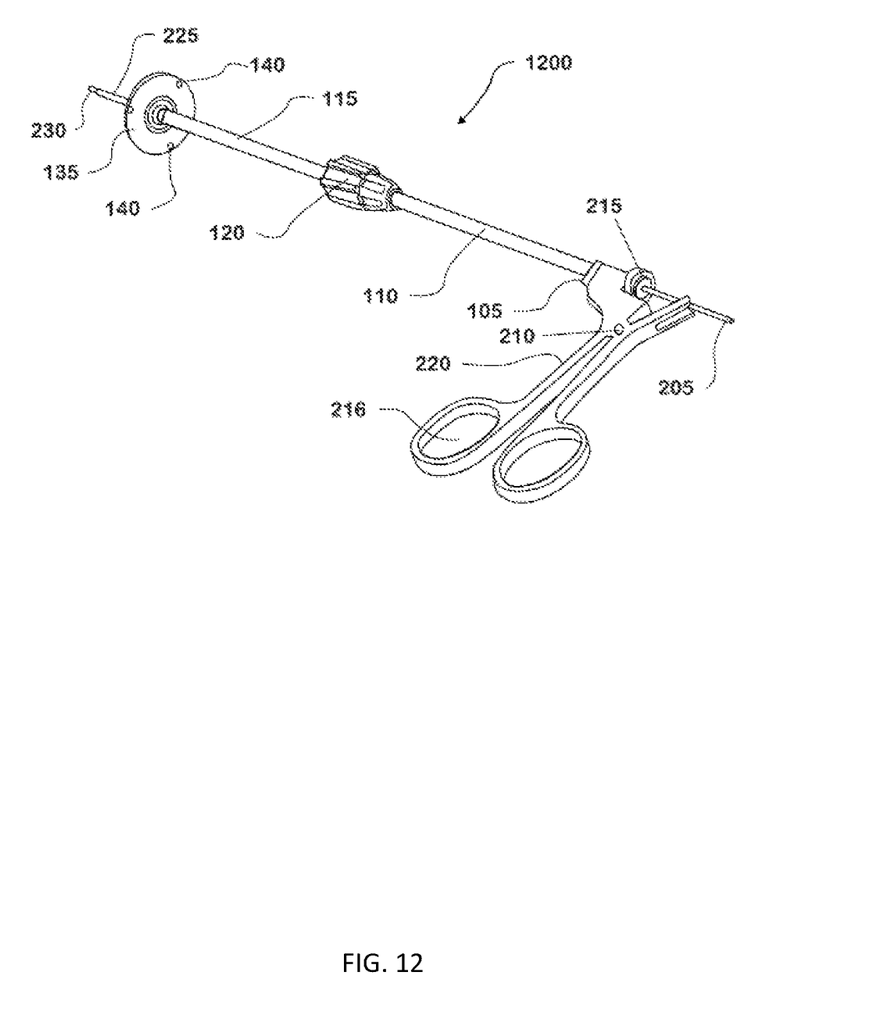
FIG. 12 is a perspective view of the strengthening device of FIG. 11, shown in a compressed position, providing rigidity to an instrument shaft.

As illustrated in FIG. 12, in use, after the percutaneous skin is penetrated by the instrument tip 230, the foot 135 protects the strengthening device 500 from sliding into the patient and also provides a resistance pressure that is used to help compress the elongated spring 405 and collapsible tube 150. As discussed above, this allows the exposed distal shaft 605 to penetrate further into the patient, while providing support to the portion of the shaft 205 outside of the patient's body.

The foot 135 pushes back minimally against the surface of the patient's skin, thereby not interfering with the normal inward and outward motion of the instrument during the procedure. This force can be adjusted to balance the device against the forces or friction and gravity, or can be reduced or increased to provide a counter force that helps control the instrument's position. The foot 135 may be fabricated of but not limited to plastics, or metal alloys. It may be secured through suture holes 140 located along the circumference. The foot 135 may be held against the skin with a force from the sleeve, or may be physically attached to the patient via sutures or adhesive materials. In the case that trocars are being used with the instrument, the foot 135 would be pressed against the trocar rather than the skin, but would be held there by the same forces and mechanisms.

Notably, the device 500 of FIGS. 11 and 12 provides a great amount of collapsibility and strengthening to an instrument used therewith. As pressure is exerted downwards on the tube 150 and spring 405, the spring 405 compresses and becomes more rigid, thereby transferring that rigidity to the shaft or medical device.

In an embodiment, the upper and lower tubes 110, 115 of the devices according to the various embodiments described above are made out of plastics, aluminum or metal alloys, although other materials may also be utilized without departing from the broader aspects of the present invention. The upper and lower tubes 110, 115 are collapsible, thus decreasing in length as greater pressure is applied permitting the elongated springs therewithin to compress and provide rigidity to the shaft or medical instrument. In an embodiment, the tubes 110, 115 may have crimped or ridged edges along their circumference that permit their lengths to collapse and conform to shorter spring length during use, as discussed above. It should be noted that the strengthening devices disclosed herein are not limited to providing rigidity and strength to just a laparoscopic instrument shaft but also other elongated instruments or devices that would benefit from increased load carrying capacity or increased rigidity.

In any of the various embodiments described above, the compression of the elongated spring provides rigidity and strength to the instrument shaft received therethrough. This is accomplished by the compression action of the spring(s), forming a wall, further limiting the movement of the shaft that is outside the patient but inside the sleeve/spring.

Importantly, the strengthening device is adapted to strengthen the shaft of an instrument extending sleeve by applying a biasing force to the shaft of the instrument. The device may be directly coupled to a proximal part of the instrument, to a port, or may be coupled directly to a patient, and may be permanently coupled to the instrument or manually coupled to the instrument as needed. The strengthening device also includes a mechanism which applies an equalizing force to the tubular member and is adjustable. As the surgical instrument is extended through the opening the medical instrument is further stabilized by the axial force applied by a ballast spring or other feature.

Moreover, as discussed hereinbefore, the swivel ball joint assembly 145 allows movement of the strengthening device 100 and shafts supported by the device 100 to pivot at different angles, permitting the distal end of the strengthening device 100 (attached to an instrument head, not shown) to reach areas inside the patient that wouldn't normally not be accessible while being supported by the foot 135.

Although this invention has been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiments disclosed in the above detailed description, but that the invention will include all embodiments falling within the scope of this disclosure.

What is claimed is:

1. A strengthening device for an instrument, comprising:
an upper tube assembly;
a lower tube assembly operatively connected to the upper tube assembly, the upper tube assembly and the lower tube assembly being configured to receive a shaft of an instrument therethrough; and
a foot pivotally connected to a distal end of the lower tube assembly, the foot including at least one of an adhesive pad and a plurality of apertures formed therethrough;
wherein at least one of the upper tube assembly and the lower tube assembly is collapsible such that a length of the at least one of the upper tube assembly and the lower tube assembly may be decreased.

2. The strengthening device of claim 1, wherein:
the upper tube assembly includes an upper tube having an upper end and a lower end;
the lower tube assembly includes a lower tube operatively connected to the lower end of the upper tube; and
wherein the lower tube assembly includes a spring disposed within the lower tube.

3. The strengthening device of claim 2, wherein:
the upper tube assembly includes a spring disposed within the upper tube.

4. The strengthening device of claim 3, further comprising:
an attachment mechanism operatively connected to the upper end of the upper tube for attaching the instrument to the device.

5. The strengthening device of claim 3, further comprising:
a locking assembly intermediate the upper tube and the lower tube and connecting the upper tube to the lower tube.

6. The strengthening device of claim 5, wherein:
the locking assembly is actuatable to selectively adjust an extent to which a distal end of the shaft protrudes beyond the foot.

7. The strengthening device of claim 2, wherein:
the upper tube and the lower tube have at least one of crimped or ridged edges along their circumference.

8. A method for supporting an instrument shaft, comprising the steps of:
inserting an instrument shaft into a sleeve having at least one collapsible tube and an elongated spring housed within the collapsible tube until a distal tip of the shaft protrudes beyond a foot connected to the sleeve;
passing the tip of the shaft through the skin of a patient until the foot comes into contact with the skin of the patient or a trocar; and
extending the tip of the shaft further beyond the foot and into the patient;
wherein extending the tip of the shaft further beyond the foot compresses the elongated spring such that the spring provides support for the shaft within the sleeve; and
wherein the foot includes at least one of an adhesive pad and a plurality of apertures formed therein.

9. The method according to claim 8, wherein:
the at least one collapsible tube includes an upper tube and a lower tube, each tube having an elongated spring housed therein.

10. The method according to claim 8, further comprising the step of:
securing the foot to the skin of the patient.

11. The method according to claim 10, further comprising the step of:
attaching an instrument having the instrument shaft to an upper end of the sleeve.

12. The method according to claim 10, further comprising the step of:
pivoting the sleeve with respect to the foot to adjust an angle of entry of the tip.

13. A strengthening device for an instrument, comprising:
a sleeve;
a spring disposed within the sleeve; and
a foot pivotally connected to a distal end of the sleeve, the foot including at least one of an adhesive pad and a plurality of apertures formed in the foot for receiving sutures;
wherein the sleeve and the spring are configured to receive a shaft of an instrument therethrough.

14. The strengthening device of claim 13, wherein:
a distal tip of the shaft is selectively extendable beyond the foot; and
wherein extending the tip of the shaft beyond the foot compresses the spring such that the spring provides support for the shaft within the sleeve.

15. The strengthening device of claim 14, further comprising:
an attachment mechanism operatively connected to an upper end of the sleeve for attaching the instrument to the device.

16. The strengthening device of claim 14, wherein:
the foot is pivotable with respect to the sleeve for adjusting an insertion angle of the shaft.

\* \* \* \* \*